United States Patent [19]

Campbell et al.

[11] 3,981,937

[45] Sept. 21, 1976

[54] DEHYDROHALOGENATION OF 3,4-DICHLORO-1-BUTENE

[75] Inventors: John B. Campbell; Robert Edward Tarney, both of Hockessin, Del.

[73] Assignee: E. I. Du Pont de Nemours and Company, Wilmington, Del.

[22] Filed: Feb. 13, 1970

[21] Appl. No.: 11,351

Related U.S. Application Data

[63] Continuation-in-part of Ser. No. 633,435, April 25, 1967, abandoned, which is a continuation-in-part of Ser. No. 554,978, June 3, 1966, abandoned.

[52] U.S. Cl. .................................. 260/655
[51] Int. Cl.² ........................................ C07C 21/20
[58] Field of Search ...................... 260/655, 567.6

[56] References Cited
UNITED STATES PATENTS 2,430,016  11/1947  Hearne .............................. 260/655
2,879,311  3/1959  Hawkins et al. .................... 260/655
3,024,283  3/1962  Metcalfe et al. ................. 260/567.6

FOREIGN PATENTS OR APPLICATIONS 657,378  4/1965  Belgium ............................. 260/655
1,055,064  1/1967  United Kingdom ................. 260/655

OTHER PUBLICATIONS

"Synthetic Detergents," McCutcheon, (1950), p. 273.

*Primary Examiner*—James O. Thomas, Jr.
*Assistant Examiner*—A. Siegel

[57] ABSTRACT

Dichlorobutene is treated with aqueous inorganic alkali in the presence of a catalytic amount of a quaternary ammonium compound catalyst to dehydrochlorinate the dichlorobutene and directly form chloroprene.

22 Claims, No Drawings

DEHYDROHALOGENATION OF 3,4-DICHLORO-1-BUTENE

PRIORITY

This application is a continuation-in-part of application Ser. No. 633,435 filed Apr. 25, 1967 now abandoned, which is a continuation-in-part of application Ser. No. 554,978 filed June 3, 1966, now abandoned.

BACKGROUND OF THE INVENTION

It is known to dehydrohalogenate halogen-containing compounds by reaction with aqueous alkali. Chloroprene (2-chloro-1,3-butadiene) has been prepared by dehydrochlorinating 3,4-dichloro-1-butene with aqueous alkaline solution such as aqueous sodium hydroxide or potassium hydroxide. Such a procedure is disclosed in U.S. Pat. No. 2,430,016. However, these processes are characterized by relatively low reaction rates, and relatively high yields of unwanted by-product 1-chloro-1,3-butadiene. There has been a need for a dehydrohalogenation process with a much faster reaction rate and lower yield of unwanted by-product than has heretofore been available.

THE INVENTION

In accordance with this invention there is provided an improvement in the aqueous process for dehydrohalogenating dichlorobutene. The process involves conducting the dehydrohalogenation in an aqueous alkali in the conventional manner with the exception that a catalytic amount of an organic quaternary ammonium compound is present. Usually the amount of quaternary compound will be about 0.01–10% by weight based on the weight of the dichlorobutene which is being dehydrohalogenated. By operating in accordance with the present invention very substantial increases in reaction rate are obtained with a higher percentage conversion as well as a reduction in the percentage of the unwanted by-products which are normally produced in aqueous dehydrohalogenation reactions. The by-product, 1-chloro-1,3-butadiene, also referred to as α-chloroprene, is undesirable since it copolymerizes with the chloroprene and introduces an undesirably high amount of allylic chlorines into the polymer backbone. The allylic chlorines are active sites which decrease the storage stability of the polymer, decrease its processing safety, and adversely affect the elongation and tensile strength of the final vulcanizate.

The temperature to be used in carrying out the process of this invention may vary from about 0°C. to about 100°C. At temperatures below about 0°C. the reaction is undesirably slow. Temperatures above 100°C. are undesirable because of increased problems of polymerization and by-product formation. The preferred temperature range is from about 40°C. to about 85°C. It is most convenient to use the autogenous pressures which develop normally under the reaction conditions. Higher or lower pressures may be used if desired. Temperatures above about 60°C. necessitate the use of elevated pressures because of the volatility of the materials in the reaction mixture.

The reaction is carried out in the absence of oxygen to avoid subsequent reactions of the chloroprene formed. Also, it is highly desirable to add polymerization inhibitors such as phenothiazine, alkyl nitrites, nitroso compounds or other compounds which inhibit polymer formation since the reactants and products are polymerizable.

The alkaline material used in the process of this invention can be any alkaline material which is capable of effecting a dehydrohalogenation by reaction with a dichlorobutene in aqueous media. Alkali metal hydroxides are preferred in carrying out the process of this invention. Sodium hydroxide is particularly preferred because of its ready availability. Other hydroxides which may be used include potassium hydroxide, lithium hydroxide, rubidium hydroxide and cesium hydroxide. Alkaline earth metal hydroxides such as calcium and barium hydroxides can also be used.

The hydroxide is preferably used as an aqueous solution, and the concentration of hydroxide in the solution may vary over a wide range. When no quaternary ammonium compound catalyst is used in the process, it is conventional that an alkali metal hydroxide be used in solution in a concentration of 1–10% by weight. As the concentration of hydroxide is increased, the reaction rate decreases and becomes impractically slow by the time the concentration has reached 25%. Surprisingly, the quaternary ammonium compound catalysts increase the conversion of dichlorobutene to chloroprene in an aqueous reaction medium having at least about 15% by weight alkaline material up to a saturated solution. Using the preferred quaternary ammonium catalysts in the process of this invention, an aqueous reaction medium having at least about 5% by weight hydroxide can be used. As used herein, the terms "percent by weight alkaline material" and "percent by weight hydroxide" refer to weight of the alkali metal hydroxide or alkaline earth metal hydroxide times 100 divided by the weight of water plus the hydroxide. The concentrations referred to are those of the solution supplied to the reaction. During the reaction hydroxide is consumed and water is formed so that the concentration of hydroxide changes during the course of the reaction.

The mole ratio of hydroxide to halo-compound can be as low as about 0.5:1. The optimum mole ratio of reactants to use will vary with the effectiveness of the quaternary ammonium compound being employed as catalyst. With preferred catalysts mole ratios of 1:1 are practical. Higher mole ratios are needed with catalysts producing lower conversions. The upper limit is not critical. In general, there is no advantage in using mole ratios above 20 to 1.

The organic quaternary ammonium compounds that may be used in practicing this invention are of many different types. The nitrogen may be substituted by four cyclic or acyclic organic radicals or may be part of a ring. The quaternary compound may contain one or more than one quaternary ammonium group. The nitrogen is attached to four radicals by covalent bonds. At least one of the radicals can be a ($C_6$–$C_{20}$) alkyl or alkenyl radical, or at least two of the radicals can be ($C_7$–$C_{20}$) aralkyl radicals. In the alternative, at least one of the radicals can be a ($C_7$–$C_{20}$) aralkyl radical having bonded thereto a ($C_6$–$C_{20}$) alkyl or alkenyl radical. As another alternative, at least one radical can be an alkyl, alkenyl, or aralkyl radical containing up to 20 carbon atoms and containing a hydroxy or ether group in a position beta or gamma to the nitrogen. The remaining radicals attached to the nitrogen of the organic quaternary ammonium compound can be ($C_1$–$C_{20}$) alkyl or alkenyl radicals or ($C_7$–$C_{20}$) aralkyl radical. Furthermore, any two of the radicals can be joined to form a ring containing the nitrogen as part of the ring. The radicals on the nitrogen may be cyclic or acyclic, branched or unbranched, saturated or unsaturated. It is not essential that these radicals be free of non-hydrocarbon substituents. However, any substituents on any of the radicals must be free of functional groups capable of forming inner salts with the quaternary ammonium ion. When the quaternary nitrogen function is part of a ring, the ring must be non-aromatic; that is, the nitrogen should be connected to four aliphatic carbon atoms by single bonds. The ring may contain only carbon atoms, or other nitrogen atoms, or other members such as oxygen or sulfur atoms. Usually, the rings contain five to seven members. Fused ring systems can be used.

In general, the catalysts increase in effectiveness as the chain length of at least one substituent on the nitrogen increases. Improved effectiveness is also imparted by an hydroxy or ether group in a position beta to the nitrogen atom.

In the quaternary ammonium compounds the anion is not critical. It may be a halogen ion, a hydroxy ion, an ethyl sulfate ion, or any anion which does not interfere with the reaction and which does not promote polymerization of the product. Most often the chloride ion is used because the chlorides are most readily available and least expensive.

The preferred catalysts for use in the present invention are (a) the compounds having the general formula $R_1R_2R_3R_4NCl$ wherein $R_1$, $R_2$ and $R_3$ are alkyl, alkenyl or aralkyl radicals of up to about 20 carbon atoms and $R_4$ is an alkyl or alkenyl radical from about 6 to 20 carbon atoms or a benzyl or a ($C_6$–$C_{20}$)alkyl- or alkenyl-substituted benzyl radical; and (b) compounds of the above structure in which at least one of $R_1$, $R_2$ and $R_3$ contains an hydroxy or ether group in a position beta to the nitrogen atom. Typical of the compounds of type (b) are those having the structure

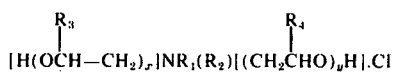

wherein $R_1$ is a ($C_6$–$C_{20}$) alkyl or alkenyl radical, $R_2$ is a ($C_1$–$C_{20}$) alkyl or alkenyl or a benzyl or ($C_1$–$C_{20}$) alkyl-substituted benzyl radical, $R_3$ is H or methyl, $R_4$ is H or methyl, and the sum of x + y ranges from about 2 to 15.

Particularly preferred quaternary ammonium salts are the following:
($C_{12}$–$C_{18}$ alkyl)(benzyl)N($CH_2CHOHCH_3$)$_2$ Cl
($C_{12}$–$C_{18}$ alkyl)(benzyl)N($CH_2CH_2OH$)$_2$ Cl
($C_{12}$–$C_{18}$ alkylbenzyl)N($CH_2CH_2OH$)$_3$ Cl The amount of quaternary ammonium compound to be used in practicing the present process varies from about 0.01 to about 10% by weight, based on the weight of the 3,4-dichloro-1-butene. In the most active compounds as little as 0.01 percent may be used with advantage. In general, more than about 10% is not required and is uneconomical.

If desired, the quaternary ammonium compound may be formed in situ. Thus amines will react with 1,4-dichloro-2-butene, an impurity usually present in 3,4-dichloro-1-butene, to form mono- and/or di-quaternary ammonium salts.

The process may be carried out by either a batch or a continuous process. The product formed may be recovered by conventional techniques. In producing 2-chloro-1,3-butadiene the reaction mass can be removed as a liquid, the aqueous and organic phases can be separated by conventional methods, and the chloroprene can be separated from dichlorobutene by distillation. Other methods will be within the scope of one skilled in the art.

Although the invention is illustrated by the dehydrochlorination of 3,4-dichloro-1-butene for convenience and because this is the most readily available halogen compound, it is equally useful for splitting off hydrogen bromide, hydrogen iodide and hydrogen fluoride from the corresponding bromine-, iodine- and fluorine-containing compounds.

EXAMPLES

In the following examples conversions are in terms of mole percent and are based on vapor phase chromatographic analyses in which area percent analyses are converted to mole percent values from predetermined calibrations. The general formula used in terms of the reaction mixture analyzed is

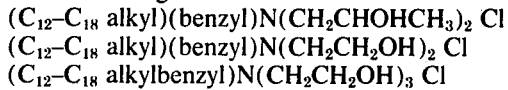

The weight percent of catalyst is based on the weight of dichlorobutene. When the catalyst is used in diluted form, percentage is based on the amount of quaternary ammonium salt present. The percent of α-chloroprene is based on the weight of 2-chloro-1,3-butadiene.

The following examples will better illustrate the nature of the present invention. All parts, percentages, and proportions are by weight unless otherwise indicated.

EXAMPLE 1

A series of experiments is carried out using the following method:

The reactor used is a jacketed 4-neck 500-ml. round-bottomed flask equipped with agitator, thermometer, reflux condenser, and nitrogen inlet tube. The flask is flushed with nitrogen and a nitrogen atmosphere is maintained throughout the reaction. 96 Grams of 21 weight percent sodium hydroxide solution and the catalyst (in the amount shown in Table I) are placed in the flask. With slow agitation, the contents of the flask are heated to 65°C. Agitation is increased to 1300 rpm and from a dropping funnel 50 grams of 3,4-dichloro-1-butene (98.6% purity) containing 0.02% by weight of phenothiazine (as a polymerization inhibitor) is introduced into the flask. The reaction is allowed to proceed at 65°C. for 60 minutes. The flask is then cooled quickly to 0°C. Cold toluene is added, the aqueous and organic phases are separated, and the aqueous phase is extracted three times with toluene. The toluene extracts are combined and analyzed by vapor phase chromatography for chloroprene and unreacted dichlorobutene.

The mole ratio of sodium hydroxide to dichlorobutene in the reaction system is 1.2 to 1.

Table I shows the results.

TABLE I

| | Group A Catalysts - General Formula $R_1(R_2)_3NX$ (Chloride used unless otherwise stated) | | | | | |
|---|---|---|---|---|---|---|
| Expt. | Catalyst $R_1$ | $R_2$ | Wt.% (Based on DCB) | Conversion % | %α-Chloroprene | Name or Source of Catalyst |
| 1 | — | — | — | 34.5 | 1.45 | Control (no additive) |
| 2 | octyl | methyl | 2 | 74.0 | 0.52 | Octyltrimethylammonium chloride |
| 3 | octyl | methyl | 3.2 | 84.2 | 0.71 | " |
| 4 | lauryl | methyl | 2 | 83.2 | 0.50 | "Aliquat" 4 (General Mills) (c) |
| 5 | palmityl | methyl | 2 | 84.3 | 0.54 | "Aliquat" 6 (c) |
| 6 | 93% octadecyl 6% hexadecyl | methyl | 2 | 84.3 | 0.43 | "Arquad" 18-50 (Armour and Co.) (a) |
| 7 | " | methyl | 5.2 | 92.8 | — | "Arquad" 18-50 (a) |
| 8 | $C_{12}$–$C_{16}$ alkyls from coconut oil | methyl | 2 | 86.3 | 0.59 | "Aliquat" 21 (c) |
| 9 | (*) | methyl | 2 | 86.1 | 0.39 | "Hyamine" 2389 (Rohm and Haas) |

(*) Mixture of methyldodecylbenzyl and methyldodecyl-α,α'-xylylene bis

| | Group B Catalysts - $R_1R_2(CH_3)_2NCl$ | | | | | |
|---|---|---|---|---|---|---|
| 10 | lauryl | lauryl | 4.95 | 96.0 | 0.19 | "Aliquat" 204 (e) |
| 11 | $C_{12}$–$C_{16}$ alkyl | benzyl | 0.16 | 74.0 | 0.52 | "Hyamine" 3500 (b) |
| 12 | $C_{12}$–$C_{16}$ alkyl | benzyl | 1.6 | 90.0 | 0.35 | "Hyamine" 3500 (b) |
| 13 | " | benzyl | 3.2 | 96.0 | 0.30 | " |
| 14 | " | benzyl | 5.6 | 97.3 | 0.33 | " |
| 15 | stearyl | benzyl | 0.33 | 69.6 | 0.55 | "Triton" X 40 (Rohm & Haas) (f) |
| 16 | alkyl from hydrogenated tallow, principally $C_{16}$ & $C_{18}$ | alkyl from hydrogenated tallow, principally $C_{16}$ & $C_{18}$ | 3 | 92.7 | 0.36 | "Aliquat" H 226 (e) |
| 17 | | | 6.82 | 97.4 | 0.38 | "Aliquat" H 226 (e) |
| 18 | benzyl | benzyl | 4 | 85.2 | 0.57 | Dibenzyldimethylammonium chloride |
| 19 | benzyl | diisobutylcresoxyethoxyethyl | 4 | 91.0 | 0.34 | "Hyamine" 10X |
| 20 | benzyl | diisobutylphenoxyethoxyethyl | 4 | 92.5 | 0.28 | "Hyamine" 1622 |

| | Group C - Miscellaneous | | | |
|---|---|---|---|---|
| Expt. | Catalyst | Wt.% | %α-Chloroprene | Conversion % |
| 21 | Methyltrioctylammonium chloride ["Aliquat" 336 (e)] | 3 | 0.43 | 97.1 |
| 22 | $(CH_3)_2\overset{R}{\underset{|}{N}}{}^+-CH_2CH_2CH_2-N^+(CH_3)_3 2Cl^-$ R = alkyl radicals from coconut oil (predominantly $C_{12}$ and $C_{14}$) "Aliquat" 721 (c) | 2 | 0.50 | 80.2 |

TABLE I-continued

| | Catalyst | | Wt.% (Based on DCB) | Conversion % | %α-Chloroprene | Name or Source of Catalyst |
|---|---|---|---|---|---|---|
| Expt. | $R_1$ | $R_2$ | | | | |

Group A Catalysts - General Formula $R_1(R_2)_3NX$
(Chloride used unless otherwise stated)

Footnotes to Table 1
(a) "Arquad" 18-50 contains 50% of the quaternary ammonium chloride, 36.5% isopropyl alcohol, and 13.5% water. The material is concentrated in vacuo before use to 100% quaternary ammonium salt content.
(b) "Hyamine" 3500 contains 80% of the quaternary ammonium compound and 20% ethanol. The alcohol has no catalytic effect under the conditions to the experiment.
(c) 50% aqueous isopropanol solution
(d) 75% aqueous isopropanol solution
(e) 82% isopropanol solution

EXAMPLE 2

This experiment is carried out in the same way as Example 1 except that potassium hydroxide (134 grams of 18 weight percent potassium hydroxide solution) is used. The molar ratio of potassium hydroxide to dichlorobutene is 1.1:1. The reaction is carried out for an hour at 65°C. The catalyst used is 0.2 percent by weight (based on dichlorobutene) of ($C_{12}$–$C_{16}$ alkyl) benzyldimethylammonium chloride ("Hyamine" 3500).

Table II shows the results.

TABLE II

| Expt. | Catalyst | Conversion % | %α-Chloroprene |
|---|---|---|---|
| 1 | None (control) | 68.5 | 1.42 |
| 2 | Alkylbenzyldimethylammonium chloride (0.2% based on dichlorobutene) | 77 | 0.83 |

EXAMPLE 3

The experiments of this example are carried out in a 250 ml. Erlenmeyer flask connected to a condenser and equipped with a magnetic stirrer. A nitrogen inlet tube is connected to the condenser. The flask is flushed with nitrogen and an atmosphere of nitrogen is maintained throughout the reaction. A solution of sodium hydroxide (which has been saturated with sodium chloride) and the catalyst are put into the flask and heated to 60°C. on a water bath. The amount of sodium hydroxide varies with concentration used in the particular experiment. In every case the amount is such as to give a mole ratio of NaOH to dichlorobutene of 10:1. 5.0 Milliliters (5.75 grams) of 3,4-dichloro-1-butene and about 0.005 gram of phenothiazine (polymerization inhibitor) are added to the contents of the flask. Agitation is begun and kept up throughout the reaction. The temperature is maintained at 60°C. After a reaction time of 15 minutes the reaction mixture is diluted with cold water (0°–5°C.) or cold saturated sodium chloride solution to bring the total volume to 200–225 ml. The contents of the flask are then extracted with 10 ml. of toluene. The toluene solution is analyzed by vapor phase chromatography.

The catalysts used in this example have the following general formula

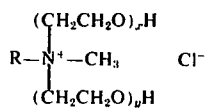

The results are shown in Table III.

TABLE III

| Catalyst | | | 5% NaOH [a] | | | 15% NaOH [a] | | |
|---|---|---|---|---|---|---|---|---|
| R= | x+y | Wt.% | Expt. | Conversion % | %α-Chloroprene | Expt. | Conversion % | %α-Chloroprene |
| oleyl | 2[b] | 1.7 | 1 | 57 | 0.89 | 8 | 80 | 0.46 |
| oleyl | 15 | 1.7 | 2 | 41 | 1.11 | 9 | 80 | 0.38 |
| stearyl | 2[b] | 1.7 | 3 | 59 | 0.99 | 10 | 79 | 0.46 |
| stearyl | 15 | 1.7 | 4 | 51 | 0.98 | 11 | 81 | 0.38 |
| $C_{12}$–$C_{16}$ alkyls from Coconut oil | 2[b] | 1.7 | 5 | 48 | 0.99 | 12 | 75 | 0.39 |
| | 15 | 1.7 | 6 | 49 | 0.93 | 13 | 86 | 0.35 |
| Control (no catalyst) | — | — | 7 | 29 | 1.38 | 14 | 12 | 1.53 |

[a] Based on weight of NaOH plus water.
[b] 75% solution in isopropyl alcohol.

EXAMPLE 4

This example is carried out in essentially the same way as Example 3 using 15% NaOH. The weight % of catalyst based on dichlorobutene is about 1.7. The catalysts tested have the general formula

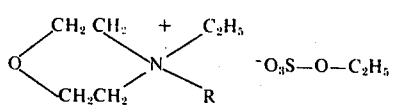

TABLE IV

| Expt. | R | Conversion % | %α-Chloroprene |
|---|---|---|---|
| 1 | cetyl | 59 | 0.70 |
| 2 | soya (mixture of $C_{18}$ mixed saturated and unsaturated aliphatic radicals) | 49 | 0.82 |

EXAMPLE 5

This example is carried out in essentially the same way as Example 3 using 15 weight % NaOH. About 1.7 wt. % of the catalyst is used based on the dichlorobutene. The catalysts used have the following general structure:

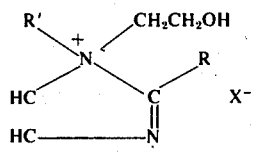

TABLE V

| Expt. | R | R' | X | Conversion % | %α-Chloroprene |
|---|---|---|---|---|---|
| 1 | heptadecenyl | ethyl | Br | 63 | 0.56 |
| 2 | Mixed $C_{11-17}$ | benzyl | Cl | 32 | 1.08 |
| 3 | Mixed unsat'd. $C_{17}$ (one and two double bonds) | benzyl | Cl(a) | 25 | 0.99 |
| 4 | heptadecenyl | benzyl | Cl(a) | 28 | 0.69 |

(a) 60% active ingredient in isopropyl alcohol.

EXAMPLE 6

This example is carried out in the same way as Example 3 using 40 weight % sodium hydroxide and oleylmethyldiethanolammonium chloride as catalyst. The mole ratio of sodium hydroxide to dichlorobutene is 9.9:1. The charge to the flask is:

| | Grams |
|---|---|
| 3,4-dichloro-butene (98.5% pure) | 11.5 (10 ml.) |
| 40% sodium hydroxide | 90.1 (63 ml.) |
| sodium chloride | 5 |
| catalyst | varied |

A small amount of phenothiazine is present as polymerization inhibitor. The reaction is carried out at 60°C. for 15 minutes except for the control, which is allowed to react for 30 minutes. The reaction mixture is diluted with 100 ml. of cold water and extracted with 20 ml. of toluene.

Table VI shows the results.

TABLE VI

| Expt. | Wt. % Catalyst | Conversion % | %α-Chloroprene |
|---|---|---|---|
| 1 | none | 1 | — |
| 2 | 0.05 | 57 | 0.24 |
| 3 | 0.11 | 86 | 0.27 |
| 4 | 0.22 | 99.9 | 0.42 |
| 5 | 0.44 | 99.9 | 0.33 |

EXAMPLE 7

This example employs the procedure of Example 3 using 15% sodium hydroxide and 1.7 weight percent of two different catalysts as shown in Table VII, which gives the results.

TABLE VII

| Expt. | Catalyst | Conversion % | % α-Chloroprene |
|---|---|---|---|
| 1 | Bis-quaternary compound prepared by reacting dodecylbenzyl chloride with the following compound [(HOCH$_2$CH$_2$)$_2$NCH$_2$CH$_2$]$_2$NCH$_2$C-H$_2$OH | 98.5 | 0.32 |
| 2 | (dodecylbenzyl)tris(2-hydroxyethyl)-ammonium chloride | 99.9 | 0.42 |

EXAMPLE 8

This example is carried out in the same way as Example 1 but using as the quaternary ammonium compound ($C_{12}$–$C_{18}$ alkyl)(benzyl)N(CH$_2$CHOHCH$_3$)$_2$·Cl. Also, the ratio sodium hydroxide/dichlorobutene is 1.1 and the reaction is carried out at 58°C. for 60 minutes using the quaternary ammonium catalyst in the amount of 0.2% by weight based on dichlorobutene. An unusual and very beneficial characteristic of this particular catalyst is its activity in dilute alkali; as the reaction proceeded with the resultant decrease in alkali concentration the catalyst remains active and effective in promoting the reaction. The conversion is 99% and the percent α-chloroprene is 0.23.

Similarly effective results are obtained using corresponding quaternary ammonium compounds in which the benzyl group is replaced by methyl, ethylbenzyl, propenyl or pentenyl groups.

EXAMPLE 9

This Example is carried out using the same general procedure of Example 3 except that the sodium hydroxide is not saturated with sodium chloride. Ten percent NaOH and a mole ratio of NaOH to dichlorobutene of 1.1:1 are used. The catalyst concentration is 2%. Table VIII shows the catalyst, the conversions, and the percent α-chloroprene in the product. The reaction is carried out for 30 minutes at 50°C.

TABLE VIII

| Catalyst | Conversion % | 60% α-Chloroprene |
|---|---|---|
| (dodecylbenzyl)N(CH$_2$CH$_2$OH)$_3$·Cl$^-$ | 90 | 0.22 |
| (C$_{12}$–C$_{18}$alkyl)N±CH$_2$CH$_2$OCH$_2$CH$_2$OH·Cl$^-$ with CH$_2$CH$_2$OH and benzyl | 91 | 0.21 |
| (dodecylbenzyl)N(CH$_3$)$_2$·Cl$^-$ with CH$_2$CH$_2$OH | 80 | 0.27 |

EXAMPLE 10

This Example is carried out using the same general procedure of Example 3 except that 10% NaOH and a mole ratio of NaOH to dichlorobutene of 1.5 are used. The reaction is carried out at 60°C. for 10 minutes. The catalyst concentration is 1%. The catalysts have the following general structure:

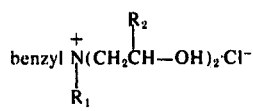

Table IX shows the conversions and percent α-chloroprene in the product for each catalyst.

TABLE IX

| Catalyst | Conversion % | % α-Chloroprene |
|---|---|---|
| R$_1$ = C$_{12}$–C$_{18}$ alkyl, R$_2$ = H | 85 | 0.27 |
| R$_1$ = C$_{12}$–C$_{18}$ alkyl, R$_2$ = CH$_3$ | 90 | 0.21 |
| R$_1$ = C$_{10}$–C$_{18}$ alkyls and alkenyl from tallow, R = H | 70 | 0.47 |
| R = oleyl (C$_{18}$alkenyl), R = H | 88 | 0.27 |
| Control (No catalyst) | 3.1 | (not measured) |

I claim:

1. In a process for directly producing 2-chloro-1,3-butadiene by reacting 3,4-dichloro-1-butene with an aqueous solution containing at least about 15% by weight of alkaline material selected from the group consisting of alkali metal hydroxides and alkaline earth metal hydroxides the improvement of obtaining very substantial increases in reaction rate with a higher percentage conversion and a reduction in the percentage of the unwanted by-product, alpha-chloroprene, by carrying out the process at a temperature of about 0°–100°C and in the presence of from about 0.01% to 10% by weight, based on the weight of 3,4-dichloro-1-butene, of an organic quaternary ammonium compound catalyst in which the nitrogen is attached to four radicals by covalent bonds wherein:
   a. at least one of the radicals is a (C$_6$–C$_{20}$) alkyl or alkenyl radical or at least two of the radicals are (C$_7$–C$_{20}$) aralkyl radicals, or
   b. at least one of the radicals is a (C$_7$–C$_{20}$) aralkyl radical having bonded thereto a (C$_6$–C$_{20}$) alkyl or alkenyl radical, or
   c. at least one radical is an alkyl, alkenyl, or aralkyl radical containing up to 20 carbon atoms and containing a hydroxy or ether group in a position beta to the nitrogen, and
   d. the remaining radicals are (C$_1$–C$_{20}$) alkyl or alkenyl radicals, or (C$_7$–C$_{20}$) aralkyl radicals.

2. The process of claim 1 in which any two of said radicals are joined to form a ring containing said nitrogen.

3. The process of claim 1 in which the alkaline material is an alkali metal hydroxide.

4. The process of claim 3 wherein the mole ratio of alkali metal hydroxide to 3,4-dichloro-1-butene ranges from about 0.5:1 to 20:1.

5. The process of claim 4 wherein the alkali metal hydroxide is sodium hydroxide.

6. The process of claim 3 wherein the quaternary ammonium compound has the general formula R$_1$R$_2$R$_3$R$_4$NCl wherein R$_1$, R$_2$ and R$_3$ are alkyl, alkenyl, or aralkyl radicals of up to about 20 carbon atoms and R$_4$ is an alkyl or alkenyl radical having from about 6 to 20 carbon atoms or a benzyl or a (C$_6$–C$_{20}$) alkyl- or alkenyl-substituted benzyl radical.

7. The process of claim 6 wherein the quaternary ammonium compound is trioctylmethyl ammonium chloride.

8. The process of claim 6 wherein R$_1$ and R$_2$ are methyl, R$_3$ is C$_{12}$ to C$_{16}$ alkyl radicals and R$_4$ is benzyl.

9. The process of claim 6 wherein at least one of R$_1$, R$_2$ and R$_3$ contains a hydroxy or ether group in a position beta to the nitrogen atom.

10. The process of claim 3 wherein the quaternary ammonium compound has the general formula

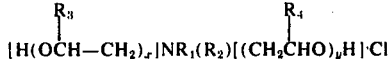

wherein R$_1$ is a (C$_6$–C$_{20}$) alkyl or alkenyl radical, R$_2$ is a (C$_1$–C$_{20}$) alkyl or alkenyl or a benzyl or (C$_1$–C$_{20}$) alkyl-substituted benzyl radical, R$_3$ is H or methyl, R$_4$ is H or methyl, and the sum of $x + y$ ranges from about 2 to 15.

11. The process of claim 3 wherein the quaternary ammonium compound has the formula

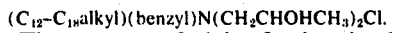

12. The process of claim 3 wherein the quaternary ammonium compound has the formula

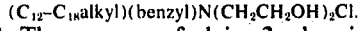

13. The process of claim 3 wherein the quaternary ammonium compound has the formula

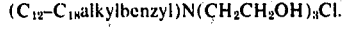

14. In a process for directly producing 2-chloro-1,3-butadiene with an aqueous solution containing at least about 5% by weight of alkaline material selected from the group consisting of alkali metal hydroxides and alkaline earth metal hydroxides, the improvement of obtaining very substantial increases in reaction rate with a higher percentage conversion and a reduction in the percentage of the unwanted by-product, alpha-chloroprene, by carrying out the process at a temperature of about 0°–100°C and in the presence of from about 0.01% to 10% by weight, based on the weight of 3,4-dichloro-1-butene, of an organic quaternary ammonium compound catalyst in which the nitrogen is attached to four radicals by covalent bonds wherein:
   a. at least one of the radicals is a $(C_6-C_{20})$ alkyl, alkenyl, or aralkyl radical, and
   b. at least one radical is an alkyl, alkenyl, or aralkyl radical containing up to 20 carbon atoms and containing a hydroxy or ether group in a position beta to the nitrogen, and
   c. the remaining radicals are $(C_1-C_{20})$ alkyl or alkenyl radicals or $(C_7-C_{20})$ aralkyl radicals.

15. The process of claim 14 in which the alkaline material is an alkali metal hydroxide.

16. The process of claim 15 wherein the mole ratio of alkali metal hydroxide to 3,4-dichloro-1-butene ranges from about 0.5:1 to 20:1.

17. The process of claim 16 wherein the alkali metal hydroxide is sodium hydroxide.

18. The process of claim 15 wherein the quaternary ammonium compound has the general formula

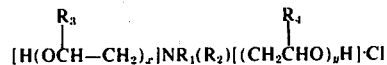

wherein $R_1$, $R_2$ and $R_3$ are alkyl, alkenyl, or aralkyl radicals of up to about 20 carbon atoms and $R_4$ is an alkyl or alkenyl radical having from about 6 to 20 carbon atoms or a benzyl or $(C_6-C_{20})$ alkyl- or alkenyl-substituted benzyl radical and wherein at least one of $R_1$, $R_2$ and $R_3$ contains a hydroxy or ether group in a position beta to the nitrogen atom.

19. The process of claim 15 wherein the quaternary ammonium compound has the general formula $$[H(OCH-CH_2)_x]NR_1(R_2)[(CH_2CHO)_yH]\cdot Cl$$

with $R_3$ above the left chain and $R_4$ above the right chain, wherein $R_1$ is a $(C_6-C_{20})$ alkyl or alkenyl radical, $R_2$ is a $(C_1-C_{20})$ alkyl or alkenyl or a benzyl or $(C_1-C_{20})$ alkyl-substituted benzyl radical, $R_3$ is H or methyl, $R_4$ is H or methyl, and the sum of $x + y$ ranges from about 2 to 15.

20. The process of claim 15 wherein the quaternary ammonium compound has the formula

21. The process of claim 15 wherein the quaternary ammonium compound has the formula

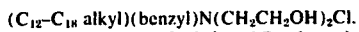

22. The process of claim 15 wherein the quaternary ammonium compound has the formula

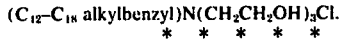

* * * * *